United States Patent [19]

Willms et al.

[11] Patent Number: 5,756,346
[45] Date of Patent: May 26, 1998

[54] PROCESS FOR THE ENZYMATIC RESOLUTION OF 2-AMINO-4-METHYL-PHOSPHINOBUTYRIC ACID DERIVATIVES

[75] Inventors: Lothar Willms, Hillscheid; Gerd Fülling, Frankfurt; Reinhold Keller, Bad Soden, all of Germany

[73] Assignee: Hoechst Aktiengesellschaft, Frankfurt, Germany

[21] Appl. No.: 589,999

[22] Filed: Jan. 23, 1996

Related U.S. Application Data

[63] Continuation of Ser. No. 324,536, Oct. 18, 1994, abandoned, which is a continuation of Ser. No. 182,668, Jan. 14, 1994, abandoned, which is a continuation of Ser. No. 18,460, Feb. 16, 1993, abandoned, which is a continuation of Ser. No. 474,499, Feb. 2, 1990, abandoned.

[30] Foreign Application Priority Data

Feb. 6, 1989 [DE] Germany ................ 39 03 446.1

[51] Int. Cl.⁶ .................... C12P 41/00; C12P 13/04; C07C 231/16
[52] U.S. Cl. .................... 435/280; 435/131; 435/106; 435/874; 435/876
[58] Field of Search .................... 435/280, 131, 435/106, 874, 876

[56] References Cited

U.S. PATENT DOCUMENTS

| | | | |
|---|---|---|---|
| 4,389,488 | 6/1983 | Graldey et al. ................ | 435/106 X |
| 4,859,602 | 8/1989 | Zimmermann et al. ........... | 435/280 |
| 5,010,012 | 4/1991 | Wullbrandt et al. ............ | 435/280 |

FOREIGN PATENT DOCUMENTS

| | | | |
|---|---|---|---|
| 0 018 415 | 10/1982 | European Pat. Off. | |
| 0 238 954 | 9/1987 | European Pat. Off. | |
| 0 292 918 | 11/1988 | European Pat. Off. | |
| 301391 | 2/1989 | European Pat. Off. | 435/106 |
| 382113 | 8/1990 | European Pat. Off. | 435/106 |
| 29 39 269 | 7/1982 | Germany. | |
| 248191 | 12/1985 | Japan | 435/128 |

OTHER PUBLICATIONS

Plaskie et al., Substrate Specificity of Penicillin Acylase of *E. coli*, The Journal of Antibiotics, vol. XXXI No. 8, pp. 783, 786 and 787, Aug. 1978.

M. Dixon, E. C. Webb, "Enzymes" 2d Ed., Longmans, Green & Co., Ltd., London 1964, pp. 346–352).

*Primary Examiner*—Shailendra Kumar
*Attorney, Agent, or Firm*—Frommer Lawrence & Haug LLP

[57] ABSTRACT

L-PTC (L-phosphinothricin, L-2-amino-4-methylphosphino-butyric acid) is the active herbicidal component of D,L-PTC and can be obtained according to the invention when D,L-PTC derivatives which are N-acylated and esterified on the phosphinic acid group as well as optionally esterified or amidated on the carboxylic group, are treated with a hydrolytically active enzyme in an aqueous or aqueous-organic medium, in which process the L-PTC derivatives are selectively hydrolyzed on the N-acyl group or the modified carboxyl group, the resulting product mixture is resolved, and the desired L-PTC derivative is hydrolyzed to give the L-PTC and isolated by customary methods.

8 Claims, No Drawings

PROCESS FOR THE ENZYMATIC RESOLUTION OF 2-AMINO-4-METHYL-PHOSPHINOBUTYRIC ACID DERIVATIVES

This application is a continuation of application Ser. No. 08/324,536, filed Oct. 18, 1994, now abandoned which in turn is a continuation of application Ser. No. 08/182,668, filed Jan. 14, 1994, now abandoned which in turn is a continuation of application Ser. No. 08/018,460, filed Feb. 16, 1993, now abandoned, which in turn is a continuation of application Ser. No. 07/474,499, filed Feb. 2, 1990, now abandoned.

DESCRIPTION

DE-A-2,939,269 (U.S. Pat. No. 4,226,941) and DE-A-2,717,440 (U.S. Pat. No. 4,168,963) disclose that the herbicidal action of racemic phosphinothricin or its salts with organic or inorganic bases or acids originates from L-2-amino-4-methylphosphinobutyric acid (named L-phosphinothricin or L-PTC in what follows) or salts thereof. The D-form is virtually inactive. In contrast to the readily accessible racemate of phosphinothricin, L-PTC could hitherto only be obtained by comparatively complicated processes. There seemed to be a need to develop a useful process by which the L-form can be made accessible in an economical way.

It has already been disclosed that L-PTC can be obtained by acid hydrolysis (JP-A-73-85538) or by enzymatic degradation (JP-A-74-31890) of L-PTC-alanyl-alanine, an antibiotic which is known from the literature and obtained by microbial synthesis.

Furthermore, processes are known which are based on the enzymatic resolution of racemates of chemically synthesized racemic PTC precursors. DE-A 2,939,269 describes a process in which N-acyl-PTC, in particular N-acetyl-PTC, is cleaved with the aid of acylases which can be obtained by specifically bred strains of microorganisms of the genus Pseudomonas, Streptomyces or Aspergillus. In this process, N-acyl-L-PTC is cleaved more rapidly than N-acyl-D-PTC. According to the information given by DE-A 2,939,269, the acylases used have hardly any, or only very little, effect on substrates other than N-acyl-L-PTC, for example on N-acyl derivatives of customary L-amino acids.

In contrast, DE-A-3,048,612 (U.S. Pat. No. 4,389,488) claims that commercially available acylases are usually not successful at the attempt to cleave rac-acyl-PTC. In this context, DE-A-3,048,612 describes an advantageous individual case, according to which the activity and selectivity of penicillin acylase (pen-G-acylase) is improved when phenacetyl-PTC is used. This was also surprising insofar as, according to A. Plaskie, J. Antibiotics 31, 783 (1978), it was expected that a variation on the amino acid moiety of the substrate in comparison with phenacetylated simple natural amino acids, such as phenacetylalanine or phenacetylvalin, would result in a sharp decrease in the pen-G-acylase activity or selectivity for deacylation of the L-isomer.

DE-A 2,927,534 (U.S. Pat. No. 4,389,489) or DE-A 2,215,853 (U.S. Pat. No. 3,813,317) discloses the resolutions of racemates of natural and synthetic amino acids, in particular aryl-substituted amino acids, by means of carboxylic ester cleavage with the aid of proteolytic enzymes, in which case, again, it is the L-enantiomer which is preferentially reacted enzymatically. However, it should be noticed that no mention is made in any of the cited publications that it might be possible to cleave amino acids having a phosphorus-containing radical. This is probably due to the fact that P(V)-containing compounds, in particular derivatives of the general formula R'R"P(O)OR''' simulate the transitional state of an enzymatically hydrolyzed carboxylic ester because of their sterical arrangement (see M. Dixon, E. Webb in "Enzymes" e. Edition, Longmans, Grenn & Co. LTD, London 1964, P. 346–352) and, accordingly, could have a deactivating influence on hydrolytically active enzymes. In fact, DE-A 3,048,612 did indeed describe the fact that proteolytic enzymes which have esterase activity and which are highly active and selective in the case of conventional D,L-amino acids, have no, or only a greatly reduced, activity in the case of D,L-PTC esters.

On the basis of the prior art which has been mentioned, it could not have been predicted that an effective enzymatic resolution of racemates could be carried out using readily accessible, diprotected or triprotected PTC derivatives which are modified on the phosphinic acid moiety of the PTC.

The invention relates to a process for the enzymatic resolution of PTC derivatives, which comprises treating a mixture of D- and L-PTC derivatives of the general formula (I)

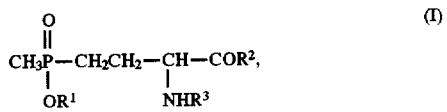

in which a) $R^1$ is unbranched or branched $C_1$–$C_{20}$-alkyl which is unsubstituted or substituted by one or more halogen radicals, such as fluorine, chlorine, bromine or iodine, or monosubstituted or polysubstituted by $C_1$–$C_8$-alkoxy, or $R^1$ is $C_3$–$C_8$-cyclo-alkyl which can be substituted by one or more groups from the series comprising $C_1$–$C_4$-alkyl, $C_1$–$C_4$-alkoxy and halogen, or $R^1$ is $C_3$–$C_{10}$-alkenyl, $C_3$–$C_{10}$-alkynyl or benzyl, $R^2$ is hydroxyl, unbranched or branched $C_1$–$C_{20}$-alkoxy which is unsubstituted or substituted by one or more halogen radicals, such as fluorine, chlorine, bromine and iodine, or monosubstituted or polysubstituted by $C_1$–$C_8$-alkoxy, or $R^2$ is amino or ($C_1$–$C_{20}$-alkyl) amino, and $R^3$ is formyl, unbranched or branched ($C_1$–$C_{20}$-alkyl) carbonyl which is unsubstituted or substituted in the alkyl moiety by one or more radicals from the series comprising hydroxyl, halogen, $C_1$–$C_4$-alkoxy, $C_1$–$C_4$-alkylthio, and phenyl which can be substituted by up to three radicals from the group comprising $C_1$–$C_{12}$-alkyl, $C_1$–$C_{12}$-alkoxy, halogen, nitro and $CF_3$, or $R^3$ is benzoyl or benzoyl which is substituted by 1 to 3 radicals from the group comprising $C_1$–$C_{12}$-alkyl, $C_1$–$C_{12}$-alkoxy, halogen, nitro and $CF_3$, or b) $R^1$ is as defined for a), $R^2$ is as defined for a), but is not hydroxyl, and $R^3$ is as defined for a), or is another protective group customary in the case of amino groups, in particular selected from amongst unbranched or branched ($C_1$–$C_{20}$-alkoxy) carbonyl and $C_1$–$C_{20}$-alkylsulfonyl, each of which is unsubstituted or substituted in the alkyl moiety by one or more radicals from the group comprising hydroxyl, halogen, $C_1$–$C_4$-alkoxy, $C_1$–$C_4$-alkylthio, phenyl, phenyl which has 1 to 3 substituents selected from the group comprising $C_1$–$C_{12}$-alkyl, $C_1$–$C_{12}$-alkoxy, halogen, nitro and $CF_3$, and phenylsulfonyl which can be substituted by up to three radicals from amongst $C_1$–$C_{12}$-alkyl, $C_1$–$C_{12}$-alkoxy, halogen, nitro and $CF_3$, with a hydrolytically active enzyme in an aqueous or aqueous-organic medium, where, in case a), it is preferred to use an enzyme which cleaves N-acyl groups (acylase) and, in case b), it is preferred to use a proteolytic or esterase-active enzyme.

A process according to the invention is of particular interest, and it comprises using a mixture of D- and L-PTC derivatives of the indicated formula (I), in which a) $R^1$ is unbranched or branched $C_1$–$C_{10}$-alkyl or $C_1$–$C_{10}$-alkyl which is substituted by halogen, such as fluorine or chlorine, or by $C_1$–$C_4$-alkoxy, or $R^1$ is $C_5$–$C_6$-cycloalkyl, $R^2$ is hydroxyl, unbranched or branched $C_1$–$C_8$-alkoxy or $C_1$–$C_8$-alkoxy which is monosubstituted or polysubstituted by halogen, such as fluorine and chlorine, or by $C_1$–$C_4$-alkoxy, or $R^2$ is amino or $(C_1$–$C_{10})$-alkylamino, and $R^3$ is formyl, unbranched or branched ($C_1$–$C_{10}$-alkyl) carbonyl which is unsubstituted or substituted in the alkyl moiety by one or two radicals from the group comprising hydroxyl, halogen, phenyl, $C_1$–$C_4$-alkoxy, $C_1$–$C_4$-alkylthio, and a phenyl radical which is substituted by 1 to 3 radicals selected from amongst $C_1$–$C_4$-alkyl, $C_1$–$C_4$-alkoxy and halogen, or $R^3$ is benzoyl or benzoyl which is substituted by 1 to 3 radicals selected from amongst $C_1$–$C_4$-alkyl, $C_1$–$C_4$-alkoxy and halogen, or b) $R^1$ is as defined for a), $R^2$ is as defined for a), but is not hydroxyl, and $R^3$ is as defined for a) or is $(C_1$–$C_{10}$-alkoxy)carbonyl which is unsubstituted or substituted by hydroxyl, halogen, methoxy, ethoxy, phenyl, or a phenyl radical which carries one to three substituents from the group comprising $C_1$–$C_4$-alkyl, $C_1$–$C_4$-alkoxy and halogen.

A process according to the invention which comprises using a mixture of D- and L-PTC derivatives of the indicated formula (I), in which a) $R^1$ is unbranched or branched $C_1$–$C_6$-alkyl or is cyclohexyl, $R^2$ is hydroxyl, unbranched or branched $C_3$–$C_6$-alkoxy, preferably methoxy or ethoxy, or amino, and $R^3$ is $(C_1$–$C_4$-alkyl)carbonyl, preferably acetyl, or $(C_1$–$C_4$-alkyl)carbonyl which is substituted by phenyl or by phenyl which is monosubstituted to trisubstituted and whose 1 to 3 substituents are selected from amongst $C_1$–$C_4$-alkyl, $C_1$–$C_4$-alkoxy and halogen, preferably phenacetyl, or $R^3$ is benzoyl, or b) $R^1$ is unbranched or branched $C_1$–$C_6$-alkyl or is cyclohexyl, $R^2$ is unbranched or branched $C_1$–$C_6$-alkoxy, or amino, and $R_3$ is as defined for a) or is unbranched or branched $(C_1$–$C4$-alkoxy)carbonyl, preferably tert.-butyloxycarbonyl, or is benzyloxycarbonyl which can be additionally substituted in the phenyl ring by up to three radicals from the group comprising $C_1$–$C_4$-alkyl, $C_1$–$C_4$-alkoxy and halogen, is preferred.

$C_1$–$C_6$-alkyl is, in particular, methyl, ethyl, 1-propyl or 2-propyl, n-, i-, tert.- or 2-butyl, 3-methyl-2-butyl, n-, i-, tert.-, 2- or 3-pentyl, n-hexyl or a stereo-isomeric hexyl.

$C_1$–$C_6$-alkoxy is, in particular, $(C_1$–$C_6$-alkyl)oxy, where the alkyl radical in this case has the abovementioned meaning.

Unless defined in greater detail, halogen radicals are the radicals fluorine, chlorine, bromine and iodine, preferably fluorine and chlorine, in particular chlorine.

The resolution according to the invention can be brought about by N-acyl cleavage of the D,L-PTC derivatives of formula (I) in which $R^1$, $R^2$ and $R^3$ have the meanings given for a), or by hydrolytic enzymatic carboxyl ester cleavage or carboxamide cleavage of the corresponding D,L-PTC derivatives of the formula (I) in which $R^1$, $R^2$ and $R^3$ have the meanings given for b).

The N-acyl cleavage of the acylated a-amino group gives the corresponding L-PTC derivative where $R^3$ is H, which can be isolated from the aqueous solution of the reaction mixture in a customary manner, for example by removing the unreacted D-PTC derivative and the acid which has been cleaved off, of the formula $R^3$-OH, by extraction at a pH in the acid range with the aid of an organic solvent, in which process the L-PTC derivative remains in the aqueous solution in the form of the ammonium salt and can subsequently be isolated by evaporating the aqueous solution to dryness. Furthermore, a separation by crystallization, distillation, chromatography etc. is feasible. Alternatively, it is also possible to subject the substance mixture to alkaline hydrolysis at room temperature, for example at a pH of 12 or higher. The optical antipodes of phosphinothricin are then present in the form of free L-PTC (where $R^3$=H) or of N-acyl-D-PTC, and they can be purified as described (cf. DE-A 2,939,269 and DE-A 3,048,612 which have been mentioned).

Suitable acylases for the process according to the invention with N-acyl cleavage are those which have a sufficiently high hydrolytic activity in an aqueous or aqueous-organic medium. Such enzymes can be selected easily in preliminary experiments from the group of the customary acylases.

Suitable enzymes for the N-acyl cleavage according to the invention of phosphinic-ester-protected derivatives are, for example, acylase I (EC 3.5.1.14), in particular for N-acetyl derivatives, and penicillin-G-acylase (EC 3.5.1.11), in particular for phenacetyl derivatives. Penicillin-G-acylase sometimes has other names in the specialist literature, such as, for example, penicillin-G-amidase or pencilin-amidohydrolase.

Alternatively, it is possible to cleave the carboxylic ester function or carboxamide function enzymatically. In this case, the protected amino group in the α-position to the —CO—O— or —CO—NH— group can be protected by almost any desired N-protective group, preferably by the customary N-protective groups as are described in Th. Greene, Protective Groups in Organic Synthesis, John Wiley & Sons, New York 1981, in particular on p. 218 et seq.

Suitable enzymes for the last-mentioned case are, in particular, proteolytic or esterase-active enzymes, in particular serineproteases and thiolproteases, preferably subtilisin (EC 3.4.4.16, new classification No. EC 3.4.21.4), α-chymotrypsin (EC 2.4.4.5, new class. No. 3.4.21.1)., papain (EC 3.4.4.10, new class No. EC 3.4.22.2), ficin (EC 3.4.22.3) or bromelain (EC 3.4.22.4) the first two having a serine radical in the active center of the amino acid chain while the latter ones have cystein as an active center of the amino acid chain. Subtilisin is preferred. Likewise, technical-grade enzyme qualities can be employed as are known, for example, under the tradenames Maxatas® protease with pH range 7–11 having some esterase and amidase activity; (manufacturer: Gist-Borcades N.V., Delft/ Netherlands) and Alcalase® mainly containing subtilisin, (manufacturer: Novo Industrie AS, Copenhagen/Denmark).

The enzymatically hydrolyzed L-PTC derivative where $R^2$ is OH can be successfully isolated in a customary manner, or a manner known in principle, such as, for example, by crystallization, distillation, column chromatography or ion-exchange chromatography and, in particular, by rapid extraction, if appropriate at a reduced temperature of 0° to 10° C., of the unreacted D-PTC derivative from the aqueous phase (the preferred pH being 6–9) with the aid of a suitable organic solvent, in which process the L-PTC derivative resulting from a carboxylic ester cleavage or carboxamide cleavage remains in the aqueous phase in the form of the carboxylate salt ($R^2=O^-M^+$). In this process, the pH is to be chosen in such a way that chemical hydrolysis is not yet initiated. After the D-derivative has been separated off, the L-PTC derivative is subjected to chemical hydrolysis analogously to customary methods, for example using an aqueous dilute mineral acid at a temperature of 20° C. to the boiling point of the solution at reaction times of 1 to 24 hours. A suitable mineral acid is, for example, a hydrohalic acid or sulfuric acid, in particular dilute to concentrated hydrochloric acid. In individual cases, organic acids are also well suited. Total chemical hydrolysis gives in addition to L-PTC also the carboxylic acid which corresponds to the acyl radical $R^3$, it being possible to remove the carboxylic acid from the aqueous-acid solution by distillation or extraction using a suitable organic solvent. When the aqueous phase is then evaporated to dryness, L-PTC remains in the form of the ammonium salt.

The D-PTC derivatives which remain can optionally be subjected to further purification by extraction processes, distillation, crystallization or chromatography, and may then be purified of the by-products of the enzymatic hydrolysis, and, if appropriate after racemization, for example by thermal means or by the action of a base, for example, an alcoholate in alcoholic solution, can be resubjected to enzymatic hydrolysis as a D,L-mixture. This racemization with the base usually proceeds under conditions which are particularly mild on the substance.

Said enzymes, in free form or after immobilization, can be employed in processes which are customary or known to the expert. The specific substrate is employed in the form of a solution or suspension in aqueous medium. Possible concentrations are from 0.1% up to a saturated solution (e.g. the latter case if the process is carried out in suspension). In individual cases, it is possible to add water-soluble solvents, such as dimethylsulfoxide or methanol, and also to carry out the process in a two-phase mixture with the addition of water-insoluble organic solvents.

In general, the reaction temperature for the enzymatic cleavages is 10°–60° C., preferably 20°–50° C, in particular 20°–40° C. The process can be carried out for example batchwise or continuously as a column process.

Enzymatic hydrolysis is preferably carried out at a pH of 5 to 9, in particular pH 6 to 8.5, it being also possible to carry out the process in individual cases at pH 5 to 6 in order to suppress unspecific hydrolysis of the carboxylic ester or carboxamide.

The procedure of the reaction can be monitored via the decrease of the substrate, for example HPLC. In individual cases, in particular in the carboxylic ester cleavage, it is possible to determine the procedure of the reaction by other simple methods, for example by the amount of base which must be metered in to reach a constant pH.

The content of L-compound in the product of the enzymatic cleavage can be determined with the aid of HPLC after alkaline or acid hydrolysis to give L-PTC has been carried out, followed by derivatization by a manner known per se (D. Aswad, Analytical Biochemistry 137, 405–409 (1984)).

The starting substances of the general formula I, with the exception of those where $R^2$ is amino or alkylamino, are known or can be prepared by processes known per se (cf. JP-75-7 237; WO 79-1114; JP 73-91019; Meiji Seika Kenkyo Nempo 1981, (20) 33-8). Individual examples in this context are listed in the experimental part. Starting substances of the formula (I) in which $R^2$ is amino or alkylamino, are novel and can be prepared by selective hydrolysis and, if appropriate, N-alkylation, via the nitrile which corresponds to the carboxylic amide. The nitrites mentioned can be prepared, for example, as described in EP-A-194,521 (U.S. Pat. No. 4,692,541). The invention therefore also relates to these novel compounds, including the pure enantiomers and diastereomers thereof which come under the formula, and including mixtures of stereo-isomers.

The designation D or L in the optionally derivatized PTC derivatives only indicates the configuration on the carbon atom which is in the α-position relative to the carboxylic group and which is linked to the optionally protected amino group. Because of the additional center of chirality on the phosphorus atom in the PTC derivatives protected with $R^1$, these D- or L-PTC derivatives are usually not pure enantiomers, but mixtures of diastereomers. As has emerged surprisingly, it is essentially only the configuration on the α-carbon atom mentioned which is important for the enzymatic cleavage. After hydrolysis of the radical $R^1$, the center of chirality on the phosphorus atom is virtually lost because of the rapid exchange of protons between OH and O.

The process according to the invention for the resolution of D,L-PTC derivatives and for the preparation of L-PTC is distinguished by an effective resolution of substrate and product mixture, combined with a low amount of salt obtained as a by-product. If not desired, the D-PTC derivative which is obtained after the enzymatic resolution can be racemized readily and under mild conditions, if appropriate without previous isolation, and can therefore be used again for an enzymatic resolution.

The fact there is a possibility to use commercially available acylases for the enantioselective cleavage of the PTC derivatives when those PTC derivatives are employed which have an ester-protected P-O acid function according to the invention, is a particular, unexpected advantage. It is surprising that inhibition of the hydrolytic activity by the phosphinic ester, or even the secondary reaction, hydrolysis of the phosphinic ester, is generally not observed. The protection of the phosphinic acid as an ester has a positive impact on the reaction rate, in particular in the case of the enzymatic carboxylic ester cleavage, or, in individual cases, makes acceptance of the substrate by the enzyme possible in the first place.

Moreover, it has emerged that, in spite of the massive changes of the structural as well as chemical properties of a PTC derivative of the formula (I) in which $R^3$ is phenacetyl and which is employed according to the invention, compared with PTC which is only protected by one N-phenacetyl group, as is used in accordance with DE-A-3,048,612, an effective N-phenacetyl cleavage with pen-G-acylase combined with a reaction rate which is at least identical and in some cases increased, is likewise observed. Because of the advantages which have been mentioned for work-up, the process according to the invention is also superior in this case.

A) Starting materials

EXAMPLE A1

Ethyl D,L-(3-phenylacetamido-3-ethoxycarbonylpropyl)-methylphosphinate (Formula I: $R^1=C_2H_5$, $R^2=OC_2H_5$, $R^3=C_6H_5$—$CH_2CO$):

8.97 g (0.03 mol) of D,L-(3-phenylacetamido-3-carboxypropyl)methylphosphinic acid—prepared in accordance with JP-55-0025 (1980) or EP-A-054,897—are dissolved in a mixture of 10 ml of glacial acetic acid and 80 ml of triethyl orthoformate, and the solution is refluxed for 3 hours. The reaction mixture is rotated on a rotary evaporator and purified on a silica gel column (mobile phase $CH_2Cl_2$/methanol, 9:1). This gives 9.7 g (91% of theory) of a colorless resin.

$^1$H-NMR (CDCl$_3$): δ=7.4 ($C_6H_5$,s,5H); 6.7 (NH,t,1H); 4.65 (CH,m,1H); 3.55–4.2 (2×$CH_2CH_3$,m,4H); 3.65 ($CH_2$;s, 2H); 1.1–2.2 ($PCH_3$,$CH_2CH_2$, 2×$CH_3CH_2$,m,13 H).

EXAMPLE A2
Methyl D,L-(3-phenylacetamido-3-n-butoxycarbonylpropyl)methylphosphinate (Formula I: $R^1=CH_3$, $R^2=n$-$O$-$C_4H_9$, $R^3=C_6H_5$—$CH_2CO$—):

a) D,L-(3-phenylacetamido-3-n-butoxycarbonylpropyl) methylphosphinic acid:

50.0 g (0.167 mol) of D,L-(3-phenylacetamido-3-carboxypropyl)methylphosphinic acid are dissolved in 150 ml of n-butanol, one spatula-tip full of p-toluene sulfonic acid is added, and the mixture is then refluxed for 5 hours. The reaction mixture is subsequently evaporated and the residue is crystallized by trituration with n-heptane. This gives 50 g (84% of theory) of colorless crystals of a melting point of 90° C.

b) Methyl D,L-(3-phenylacetamido-3-n-butoxycarbonylpropyl)methylphosphinate:

10.0 g (0.28 mol) of the product obtained in A2a) are reacted analogously to Example 1 with a mixture of 10 ml of glacial acetic acid/80 ml of trimethyl orthoformate. This gives 6.0 g (58.2% of theory) of a colorless resin.

$^1$H-NMR (CDCl$_3$): δ=7.2 ($C_6H_5$,m,5H); 6.8 (NH,m,1H); 4.65 (CH,m,1H); 4.05 ($CH_2CH_2CH_3$,t,2H); 3.8 (POCH$_3$,dd, 3H); 3.7 ($CH_2$,s,2H), 0.8–2.2 ($CH_2CH_2CH_2CH_3$, PCH$_3$, $CH_2CH_2$,m, 14H).

EXAMPLE A3
Ethyl D,L-(3-phenylacetamido-3-carboxypropyl)methylphosphinate a) D,L-(3-Phenylacetamido-3-benzyloxycarbonylpropyl) methylphosphinic acid:

29.9 g (0.1 mol) of D,L-(3-phenylacetamido-3-carboxy) methylphosphinic acid are suspended in 150 ml of methanol at room temperature, and the suspension is treated with 19.2 g (0.106 mol) of tetramethylammonium hydroxide pentahydrate. The solution is evaporated on a rotary evaporator, the residue is dissolved in 250 ml of absolute DMF, and the mixture is treated with 19.3 g (0.113 mol) of benzyl bromide at 0° C. After the reaction mixture has been stirred for 18 hours at room temperature, it is stirred into 600 ml of ice-water, and the mixture is extracted several times using $CH_2Cl_2$; the $CH_2Cl_2$ extracts are subsequently dried over sodium sulfate and evaporated on a rotary evaporator, and the crude product is freed from solvent residues at 50° C. under a high vacuum. This gives 28.6 g (73.5%) of a colorless oil which is employed in the next step without further purification.

b) Ethyl D,L-(3-phenylacetamido-3-benzyloxycarbonylpropyl)methylphosphinate:

20.0 g (0.05 mol) of D,L-(3-phenylacetamido-3-benzyloxycarbonylpropyl)methylphosphinic acid are refluxed for 3 hours with 50 ml of glacial acetic acid and 150 ml of triethyl orthoformate. The reaction mixture is evaporated on a rotary evaporator, and the product is purified by chromatography on silica gel (mobile phase: ethyl acetate/methanol (8:1)). This gives 11.9 g (56.7% of theory) of the desired product which is employed in the next step without further purification.

c) Ethyl D,L-(3-phenylacetamido-3-carboxypropyl)methylphosphinate:

11.0 g (0.026 mol) of ethyl D,L-(3-phenylacetamido-3-benzyloxycarbonylpropyl)methylphosphinate are dissolved in 250 ml of ethanol, 5 g of palladium on activated carbon (5% of substance) are added, and the mixture is then hydrogenated under atmospheric pressure. After 2 hours, the catalyst is filtered off and the filtrate is evaporated on a rotary evaporator, and the residue is triturated with n-heptane. This gives 6.2 g (72.9% of theory) of colorless crystals of m.p. 112°–117° C.

EXAMPLE A4
Methyl D,L-(3-acetamido-3-methoxycarbonylpropyl) methylphosphinate:

10 g (0.05 mol) of the ammonium salt of D,L-(3-amino-3-carboxypropyl)methylphosphinic acid are suspended in 40 ml of glacial acetic acid, 50 ml of 1,1,1-trimethoxyethane are added, and the mixture is then refluxed for 3 hours. It is subsequently filtered, and the filtrate is concentrated and chromatographed on silica gel (mobile phase $CH_2Cl_2$). This gives 8.75 g (75% of theory) of the desired product in the form a yellowish oil; $^1$H-NMR (CDCl$_3$): δ=7.18 (NH,m, 1H); 4.6 (CH,m,1H); 3.75 (COOCH$_3$, s,3H); 3.7 (POCH$_3$, dd,3H), 1.5–2.2 ($CH_2CH_2$,m4H); 2.05 ($CH_3CO$—,s,3H); 1.45 (PCH$_3$,d,3H).

EXAMPLE A5
Ethyl D,L-(3-acetamido-3-ethoxycarbonylpropyl) methylphosphinate:

10 g (0.05 mol) of the ammonium salt of D,L-(3-acetamino-3-carboxypropyl)methylphosphinic acid are reacted analogously to Example A4, but using glacial acetic acid/triethyl orthoformate. This gives 8 g (57.6% of theory) of the desired product in the form of a colorless oil.

$^1$H-NMR (CDCl$_3$): δ=6.95 (NH,m,1H); 4.6 (CH,m,1H); 4.24 (COOCH$_2$CH$_3$,q,3H); 4.08 (POCH$_2$CH$_3$,m,3H); 2.07 ($CH_3$CO,s,3H); 1.8–2.2 ($CH_2CH_2$,m,4H); 1.47 (PCH$_3$,d, 3H); 1.2–1.45 (POCH$_2$CH$_3$,m,3H).

EXAMPLE A6
Cyclohexyl D,L-(3-phenylacetamido-3-aminocarbonylpropyl)methylphosphinate a) Cyclohexyl D,L-(3-phenylacetamido-3-cyanopropyl) methylphosphinate:

28.7 g (0.1 mol) of cyclohexyl D,L-(3-acetoxy-3-cyanopropyl)methylphosphinate (prepared analogously to EP-A-127,577) are added dropwise at 20° C. within 1 hour to 29.6 ml of concentrated ammonia. The reaction mixture is subsequently extracted using $CH_2Cl_2$, and the $CH_2Cl_2$ extract is dried over sodium sulfate and treated with 10.2 g (0.1 mol) of triethylamine. 15.4 g (0.1 mol) of phenylacetyl chloride are added dropwise at 0° C. After the mixture has been stirred for 18 hours at room temperature, it is treated with 50 ml of water, a pH of 5 is established using 0.5N hydrochloric acid, and the mixture is extracted using $CH_2Cl_2$. The oil which remains after the $CH_2Cl_2$ extract has been evaporated is purified by chromatography on silica gel (mobile phase $CH_2Cl_2$). This gives 27.5 g (76% of theory) of the desired product;

$^1$H-NMR (CDCl$_3$): δ=9.45 (NH,m,1H); 7.3 ($C_6H_5$,s,5H); 4.95 (CH,m,1H); 4.36 (CH,m,1H); 3.6 (CH$_2$,s,2H); 1.2–2.2 ($CH_2CH_2$,PCH$_3$,$C_6H_{10}$,m,17H).

b) Cyclohexyl D,L-(3-phenylacetamido-3-aminocarbonylpropyl)methylphosphinate:

6 g (0.0165 mol) of cyclohexyl D,L-(3-phenylacetamido-3-cyanopropyl)methylphosphinate are dissolved in 40 ml of formic acid, and HCl gas is subsequently passed in at room temperature. After 3 hours, the reaction mixture is evaporated, the residue is dissolved in methylene chloride and water, and a pH of 5 is established using sodium hydrogen carbonate.

The mixture is subsequently extracted using $CH_2Cl_2$, and the $CH_2Cl_2$ extracts are dried over $Na_2SO_4$ and evaporated on a rotary evaporator. The crude product which remains is purified by chromatography on silica gel (mobile phase $CH_2Cl_2$/MeOH, 9:1). This gives 4.18 g (66.7% of theory) of a pale yellow oil;

$^1$H-NMR (CDCl$_3$): δ=7.2 ($C_6H_5$,s,5H); 7.2 (CONH$_2$,d, 2H); 5.6 (NH,s,1H); 4.2–4.8 (2×CH,m,2H); 3.6 (CH$_2$,s,2H); 1.2–2.3 ($CH_2CH_2$,PCH$_3$,$C_6h_{10}$,m,17H).

B) Enzymatic enantio-differentiating hydrolyses

EXAMPLE B1

$$\text{CH}_3\text{PCH}_2\text{CH}_2\text{CHCOR}^2$$
with OR$^1$ and NHR$^3$ substituents; P=O.

| | R$^1$ | R$^2$ | R$^3$ |
|---|---|---|---|
| (1) | Et | OH | Phac |
| (2) | Et | OH | H |
| PTC | H | OH | H |

1.2 g of ethyl D,L-(3-phenylacetamido-3-carboxypropyl)methylphosphinate (D,L-(1)) are taken up in 40 ml of H$_2$O, and, after the pH has been adjusted to 7.8, the mixture is stirred with 0.2N aqueous ammonia solution in the presence of 2 ml of fixed penicillin-G-acylase (66 units/ml) at 35° C. The pH is kept constant by adding 0.2N aqueous ammonia solution. After 2 hours, the enzyme is filtered off, a pH of 2.5 is established using concentrated hydrochloric acid, and the remaining substrate D-(1) and phenyl acetic acid are rapidly extracted exhaustively using methyl isobutyl ketone. Evaporation of the aqueous phase to dryness under reduced pressure gives 550 mg of ethyl L-(3-amino-3-carboxypropyl)methylphosphinate hydrochloride (L-(2)), containing NH$_4$Cl as impurity; $[\alpha]_D^{22}=+8.3°$ (c=5 in H$_2$O), $^1$H-NMR (D$_{2O}$) of L-(2): $\delta$=3.9–4.3 (CH$_3$CH$_2$O, CH—NH$_2$, m, 3H); 1.8–2.4 (CH$_2$CH$_2$, m, 4H); 1.65 (P—CH$_3$, d, 3H); 1.3 (CH$_3$CH$_2$O, t, 3H).

To determine the selectivity of the enzymatic cleavage, the L-(2)-hydrochloride is first refluxed for 6 hours in 20 ml of concentrated hydrochloric acid and the product is evaporated to dryness, i.e. chemically hydrolyzed. A 10 mg sample is then dissolved in 10 ml of a buffer solution at pH 10, the solution is treated with 134 μl of a solution of 1 g of BOC-cysteine in ethanol together with 67 μl of a solution of 333 mg of o-phthalic dialdehyde in 5 ml of ethanol, and, after 10 minutes, the mixture is analyzed via HPLC (column: LiChrosorb RP-18; mobile phase: 50 mmol phosphate buffer/methanol/tetrahydrofuran: 71/28/1); R$_t$ (L-PTC)=6.0 minutes; R$_t$ (D-PTC)=6.6 minutes. The proportion of pure L-(2)-hydrochloride after the enzymatic cleavage is thus calculated indirectly via the L-PTC as at least 94%.

EXAMPLE B2

$$\text{CH}_3\text{PCH}_2\text{CH}_2\text{CHCOR}^2$$
with OR$^1$ and NHR$^3$ substituents; P=O.

| | R$^1$ | R$^2$ | R$^3$ |
|---|---|---|---|
| (3) | Et | OEt | Phac |
| (1) | Et | OH | Phac |

200 mg of ethyl D,L-(3-phenylacetamido-3-ethoxycarbonylpropyl)methylphosphinate (D,L-(3)) are suspended in 40 ml of H$_2$O, and a pH of 8 is established using 0.2N aqueous ammonia solution. After 10 mg of subtilisine have been added, the mixture is allowed to react for 2 hours at 35° C. D-(3) is extracted exhaustively from the solution using methyl isobutyl ketone. The aqueous phase is adjusted to pH 2 using concentrated hydrochloric acid and likewise extracted exhaustively using methyl isobutyl ketone. Evaporation to dryness of the aqueous phase gives 75 mg of ethyl L-(3-phenylacetamido-3-carboxypropyl)methylphosphinate (L-(1)) having an optical rotation of $[\alpha]_D^{22}=+25°$ (4% in CHCl$_3$); $^1$H-NMR (D$_2$O): $\delta$=7.3 (phenyl, 5H); 4.6-4.3 (CH—NH, m, 1H); 4.3-3.7 (CH$_3$CH$_2$O, m, 2H); 3.65 (CH$_2$C$_6$H$_5$, s, 2H); 2.4-1.5 (CH$_2$CH$_2$, m, 4H); 1.5 (P—CH$_3$, d, 3H); 1.25 (CH$_3$CH$_2$O, t, 3H).

L-(1) is taken up in concentrated hydrochloric acid, and the mixture is refluxed for 6 hours and subsequently evaporated to dryness. The proportion of L-PTC is determined via HPLC as described in Example B1: accordingly, the proportion of L-compound is at least 92%.

EXAMPLE B3

$$\text{CH}_3\text{PCH}_2\text{CH}_2\text{CHCR}^2$$
with OR$^1$ and NHR$^3$ substituents; two P=O/C=O.

| | R$^1$ | R$^2$ | R$^3$ |
|---|---|---|---|
| (3) | Et | OEt | Phac |
| (4) | Et | OEt | H |

2 g of ethyl D,L-(3-phenylacetamido-3-ethoxycarbonylpropyl)methylphosphinate (D,L-(3)) are suspended in 40 ml of H$_2$O, the pH is adjusted to 8, and the mixture is stirred at 35° C. in the presence of 2 ml of fixed penicillin-G-amidase (132 units). The pH is kept constant by adding 0.2N aqueous ammonia solution. After 2 hours, the enzyme is filtered off, the reaction solution is adjusted to pH 2 using concentrated hydrochloric acid, and unreacted substrate D-(3) and phenylacetic acid are extracted exhaustively using methyl isobutyl ketone. The aqueous phase is evaporated to dryness in vacuo, this giving 729 mg of ethyl L-(3-amino-3-ethoxycarbonyl)methylphosphinate (L-(4)) having an optical rotation of $[\alpha]_D^{22}=+15°$ (c=5 in H$_2$O), containing impurities of NH4 Cl;

$^1$H-NMR (D$_2$O): $\delta$4.5-3.75 (2×CH$_3$CH$_2$O, CHNH$_2$, m, 5H); 2.4-1.75 (CH$_2$CH$_2$, m, 4H); 1.6 (P—CH$_3$), d, 3H); 1.3+1.33 (2×CH$_3$CH$_2$O, t, 6H).

L-(4) is converted to L-PTC and analyzed as described in Example B1; accordingly, the proportion of pure L-(4) is 96%.

The substrate D-(3) which has been extracted and has not been reacted enzymatically is taken up in methyl isobutyl ketone, washed once using 1N NaOH and purified by column chromatography (CH$_2$Cl$_2$:MeOH 10:1).

Yield: 700 mg of D-(3) $[\alpha]_D^{22}=-9°$ (CHCl$_3$)

EXAMPLE B4

1.2 g (3.8 mmol) of methyl D,L-(3-phenylacetamido-3-methoxycarbonylpropyl)methylphosphinate are reacted with 1.2 g of fixed penicillin-g-amidase (240 u) in 50 ml of 0.01M aqueous potassium phosphate buffer at pH 7. After 24 hours, the enzyme is filtered off, and the filtrate is adjusted to pH 3 and extracted exhaustively using methyl isobutyl ketone. The aqueous phase is extracted to dryness, a pH of 1 is subsequently established by adding concentrated hydrochloric acid, and the mixture is refluxed for 6 hours. Evaporation to dryness gives 420 mg of L-phosphinothricin: the proportion of L-PTC, determined via HPLC analogously to Example B1, is 93%.

EXAMPLE B5

700 mg (2.95 mmol) of methyl D,L-(3-acetamido-3-methoxycarbonylpropyl)methylphosphinate are taken up in 25 ml of water and, after the addition of 700 mg of acylase I, and 0.37 ml of a 0.1M CoCl$_2$ solution, were stirred at room temperature. After 19 hours, a pH of 12 to 13 is established, and the mixture is stirred for 24 hours at room temperature. The solution is evaporated to dryness and subsequently purified by ion-exchange chromatography on an acid ion exchanger (development with H$_2$O). The PTC-containing fractions (ninhydrin test, controlled by HPLC) were combined and evaporated to dryness. This gives 250 mg of a brown powder which contains L-PTC in a proportion of more than 95% (determination via HPLC analogously to Example B1).

EXAMPLE B6

500 mg of optically pure ethyl D-(3-phenylacetamido-3-ethoxycarbonylpropyl)methylphosphinate (D-(3)), originating from an enzymatic cleavage as described in Example B2, are taken up in 15 ml of H$_2$O, a pH of 8 is established, and the mixture is then stirred at 35° C. with 2N NH$_4$OH with 1 ml of penicillin-G-acylase (66 u). When the reaction is monitored via HPLC (column: LiChrosorb RP-8, Merck Hibar; mobile phase: 1 g of TBAHS+10 g of KH$_2$PO$_4$ in 1 l of H$_2$O; pH 2.1 adjusted using H$_3$PO$_4$, +1 l of methanol, UV detector 206 nm), phenylacetic acid is no longer detectable after 48 hours. Accordingly, pen-G-acylase is only capable of splitting L-(3), but not D-(3).

EXAMPLE B7

500 mg of cyclohexyl D,L-(3-phenylacetamido-3-aminocarbonylpropyl)methylphosphinate are taken up in 20 ml of 0.5M potassium phosphate buffer of pH 8, 2 ml (130 u) of fixed pen-G-acylase are added, and the mixture is then stirred at 35° C. The pH is kept constant by continuously adding 0.2N NH$_3$ solution from a burette. After 18 hours, the enzyme is filtered off, and the filtrate is extracted exhaustively using methylene chloride. The aqueous phase is adjusted to pH 2 using concentrated hydrochloric acid, phenylacetic acid is extracted using methylene chloride, and the aqueous phase is evaporated to dryness. The residue is taken up in 20 ml of concentrated hydrochloric acid, and the solution is refluxed for 7 hours and then again evaporated to dryness.

The content of L-PTC is determined via HPLC as described in Example B1; proportion of L-PTC: 94%.

EXAMPLE B8

Racemization 100 mg of ethyl D-(3-phenylacetamido-3-ethoxycarbonylpropyl)methylphosphinate (D-(3)) having an optical rotation of $[\alpha]_D^{20}=-9°$ (CHCl$_3$) are dissolved in 12 ml of EtOH, and the solution is treated with 2 mg of sodium ethanolate. After 5 hours, the solution is evaporated to dryness. The optical rotation of the product is $[\alpha]^{22}=0°$ (CHCl$_3$)

We claim:

1. A process for the enzymatic resolution of PTC derivatives, which comprises treating a mixture of D- and L-PTC derivatives of the general formula (I)

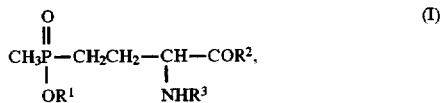

in which

R$^1$ is unbranched or branched C$_1$–C$_6$-alkyl or is cyclohexyl,

R$^2$ is hydroxyl, unbranched or branched C$_1$–C$_6$-alkoxy, or amino, and

R$^3$ is (C$_1$–C$_4$-alkyl)carbonyl, or (C$_1$–C$_4$-alkyl)carbonyl which is substituted by phenyl or by phenyl which is monosubstituted or trisubstituted and whose 1 to 3 substituents are selected from the group consisting of C$_1$–C$_4$-alkyl, C$_1$–C$_4$-alkoxy and halogen, or R$^3$ is benzoyl, or is unbranched or branched (C$_1$–C$_4$-alkoxy) carbonyl, or is benzyloxycarbonyl which additionally can be substituted in the phenyl ring by up to three radicals selected from the group consisting of C$_1$–C$_4$-alkyl, C$_1$–C$_4$-alkoxy and halogen, with a hydrolytically active acylase enzyme in an aqueous or aqueous-organic medium.

2. The process as claimed in claim 1, wherein an enzyme is used which detaches N-acyl groups.

3. The process as claimed in claim 2, wherein acylase I or pen-G-acylase is employed as the active enzyme.

4. The process as claimed in claim 1, wherein

R$^1$ is methyl, ethyl, propyl, butyl, pentyl, hexyl or cyclohexyl,

R$^2$ is hydroxyl, methoxy, ethoxy, propoxy, butoxy, pentoxy, hexoxy or NH$_2$ and R$^3$ is acetyl or phenacetyl, or is tert-butyloxycarbonyl or benzyloxycarbonyl.

5. The process as claimed in claim 1, wherein the enzymatic cleavage is carried out at a temperature of 20° to 60° C.

6. The process as claimed in claim 1, wherein enzymatically unreacted D-PTC derivative is removed after enzymatic cleavage by extraction with an organic solvent.

7. The process as claimed in claim 1, wherein L-PTC derivative obtained is subjected to chemical hydrolysis and L-PTC is isolated.

8. The process as claimed in claim 1, wherein the enzymatic cleavage is carried out at pH 5 to 9.

* * * * *